US00PP15886P3

(12) United States Plant Patent
Van Der Voort

(10) Patent No.: US PP15,886 P3
(45) Date of Patent: Jul. 19, 2005

(54) LILY PLANT NAMED SORBONNE

(50) Latin Name: *Lilium L.*
Varietal Denomination: Sorbonne

(75) Inventor: Cees A. Van Der Voort, Katwijk (NL)

(73) Assignee: Vletter & Den Haan Beheer B.V. (NL)

( * ) Notice: Subject to any disclaimer, the term of this patent is extended or adjusted under 35 U.S.C. 154(b) by 0 days.

(21) Appl. No.: 09/357,096

(22) Filed: Jul. 19, 1999

(65) Prior Publication Data

US 2002/0088034 P1 Jul. 4, 2002

(51) Int. Cl.[7] ..... A01H 5/00
(52) U.S. Cl. ..... Plt./315
(58) Field of Search ..... Plt./315

(56) References Cited

PUBLICATIONS http://www.user.netland.nl/~hanns//exit4.html, p. 4, May 1996.* http://www.user.netland.nl/~hanns//exit4.html, Aalsmeer Horticultural Sites, pp. 1–6, see p. 4, citation for 'Sorbonne', May 5, 1996.*

UPOV–ROM GTITM Computer Database 2000/02, GTI Jouve Retrieval Software, citations for 'Sorbonne'.*

UPOV–ROM GTITM Computer Database 2000/02, GTI Jouve Retrieval Software, citation for 'Sorbonne', 1993*

NL Plant Breeders Rights application LEL 1082; grant date Dec. 14, 1993.

BE Plant Breeders Rights application 25124; filing date Sep. 22, 1995.

FR Plant Breeders Rights application 0158505; filing date Sep. 4, 1995.

PL Plant Breeders Rights application LIO0027 filed Apr. 5, 1994.

DE Plant Breeders Rights application LIU00059 filed Aug. 26, 1993.

ZA Plant Breeders Rights application PT 2659 grant date Sep. 1, 2000.

* cited by examiner

*Primary Examiner*—Anne Marie Grunberg
(74) *Attorney, Agent, or Firm*—Foley & Lardner, LLP

(57) ABSTRACT

A new and distinct cultivar of Lily plant named 'Sorbonne' characterized by having soft, pinkish-red color, white flower tips, upright flowers, and vigorous growth habit.

1 Drawing Sheet

1

BACKGROUND OF THE INVENTION

The present invention comprises a new and distinct cultivar of lily plant, botanically known as *Lilium L.,* and hereinafter referred to by the cultivar name 'Sorbonne'.

'Sorbonne' is a product of a planned breeding program which had the objective of creating new lily cultivars having large, upright flowers.

'Sorbonne' was originated from a hybridization made by the inventor in a controlled breeding program in Rijnsburg, the Netherlands in 1985. The male and female parents were unnamed seedlings of *Lilium L.* oriental hybrids. Both parents are proprietary cultivars used in the breeding program.

'Sorbonne' was discovered and selected as one flowering plant within the progeny of the stated cross by the inventor, Cees A. van der Voort, on Jun. 7, 1988 in a controlled environment in Rijnsburg, the Netherlands.

The first act of asexual reproduction of 'Sorbonne' was accomplished when scales were taken from the initial selection in October 1988 in a controlled environment in Rijnsburg, the Netherlands by, or under the supervision of, Cees A. van der Voort. Horticultural examination of selected units initiated in May, 1988 has demonstrated that the combination of characteristics as herein disclosed for 'Sorbonne' are firmly fixed and are retained through successive generations of asexual reproduction.

2

BRIEF DESCRIPTION OF THE INVENTION

The following traits have been repeatedly observed and are determined to be basic characteristics of 'Sorbonne' which in combination distinguish this lily as a new and distinct cultivar:

1. soft, pinkish red-color;
2. white flower tips;
3. upright flowers; and
4. vigorous growth habit.

'Sorbonne' has not been observed under all possible environmental conditions. The phenotype of the new cultivar may vary significantly with variations in environment such as temperature, light intensity, and daylength without any change in genotype. The following observations, measurements, and values describe the new cultivar as in the experimental research station CPRO-DLO, Wageningen, the Netherlands under conditions which approximate those generally used in commercial practice.

Of the many commercial cultivars known to the present inventor, no other cultivars are similar in comparison to 'Sorbonne'.

BRIEF DESCRIPTION OF THE DRAWING

The accompanying color photographic drawing shows typical plant and flower characteristics of 'Sorbonne', with colors being as true as possible with illustrations of this type.

DETAILED BOTANICAL DESCRIPTION

In the following description, color references are made to The Royal Horticultural Society Colour Chart (R.H.S.). The color values were determined between 12 am and 2 pm in July, 1993 at the Dutch experimental research station CPRO-DLO, Wageningen, the Netherlands.

Origin: Seedling from breeding program.

Parentage:

*Female parent.*—Unnamed seedling.

*Male parent.*—Unnamed seedling.

Classification:

*Botanical.*—A hybrid of the genus *Lilium L.*

*Commercial.*—Oriental Lily cv. 'Sorbonne'.

Plant:

*Form.*—A single stem carrying numerous, alternately arranged pedicels.

*Height.*—Medium to high for the mature plant, approximately 120 cm, depending on cultivation conditions.

Growth habit: Vigorous: from the start of vegetation to the beginning of the first flowering takes 90 days depending on cultivation conditions; approximately 20–30% more vigorous than the traditional 'Stargazer' cultivar.

*Stem.*—Circular in transverse section; anthocyanin pigmentation absent; internodal length 6.8 cm, depending on the cultivation conditions of the cultivar.

*Foliage.*—Quantity: Approximately 70. Size of leaf: Average length is 10–12 cm, average width is 4 cm, depending on cultivation conditions. Shape of leaf: Generally ovate. Color: Medium green RHS 135A.

*Bulb.*—Size: 16 to 18 cm in circumference. Color: White RHS 157B with pink shades.

Bud:

*Form.*—Tapering like a lancet.

*Size.*—Medium, 11 cm in length depending on cultivation conditions.

*Opening.*—Unfolds normally.

*Color.*—Pinkish-green; light-pink, RHS 62 B, just before opening.

*Tepals.*—Folded, three visible.

Flower:

*Blooming habit.*—Raceme.

*Size.*—Medium, 20 cm in diameter depending on cultivation conditions.

*Borne.*—Upright to horizontal along a longitudinal axis.

*Shape.*—Generally, hexagonal star in form and bowl-shaped in cross-section.

*Tepalage.*—Number of Tepals: 6 Arrangement: Three inner and three outer. Color: Upper surface: Pinkish-red inner throat, RHS 64D; mid-vein is green, RHS 144D fading to white. Lower surface: Pink, RHS 62B.

*Spotting or marking.*—Spots and markings are present, dark pink in color RHS 61A.

Pedicel:

*Length.*—Medium, 10 cm long.

*Color.*—Soft pink, RHS 65A, at the tips of the tepals fading to white.

*Form.*—Tapering like a lancet.

*Texture.*—Papillose.

*Disease resistance.*—Average in comparison to the disease resistance level of traditional Lily cultivars.

*Fragrance.*—Weak.

*Lasting quality.*—Excellent; i.e., the average lasting period is at least 21 days, when cut and kept in a controlled climate in conformity with Dutch Auctions and Research Station standards.

Reproductive organs:

*Stamens and anthers.*—Arrangements: Anthers form a generally circular pattern at their upper ends. Number: 6. Length: Medium length depending on cultivation conditions. Filaments Color: Green RHS 145D.

*Pollen color.*—Orange-brown RHS 173B.

*Anther color.*—Orange-brown RHS 173B.

*Pistils.*—Green RHS 143C.

*Stigma.*—Purple RHS 186B.

*Ovaries.*—Triangular in shape.

I claim:

1. A new and distinct cultivar of Lily plant named 'Sorbonne' having a vigorous growth habitat and upright, pink flowers, as illustrated and described herein.

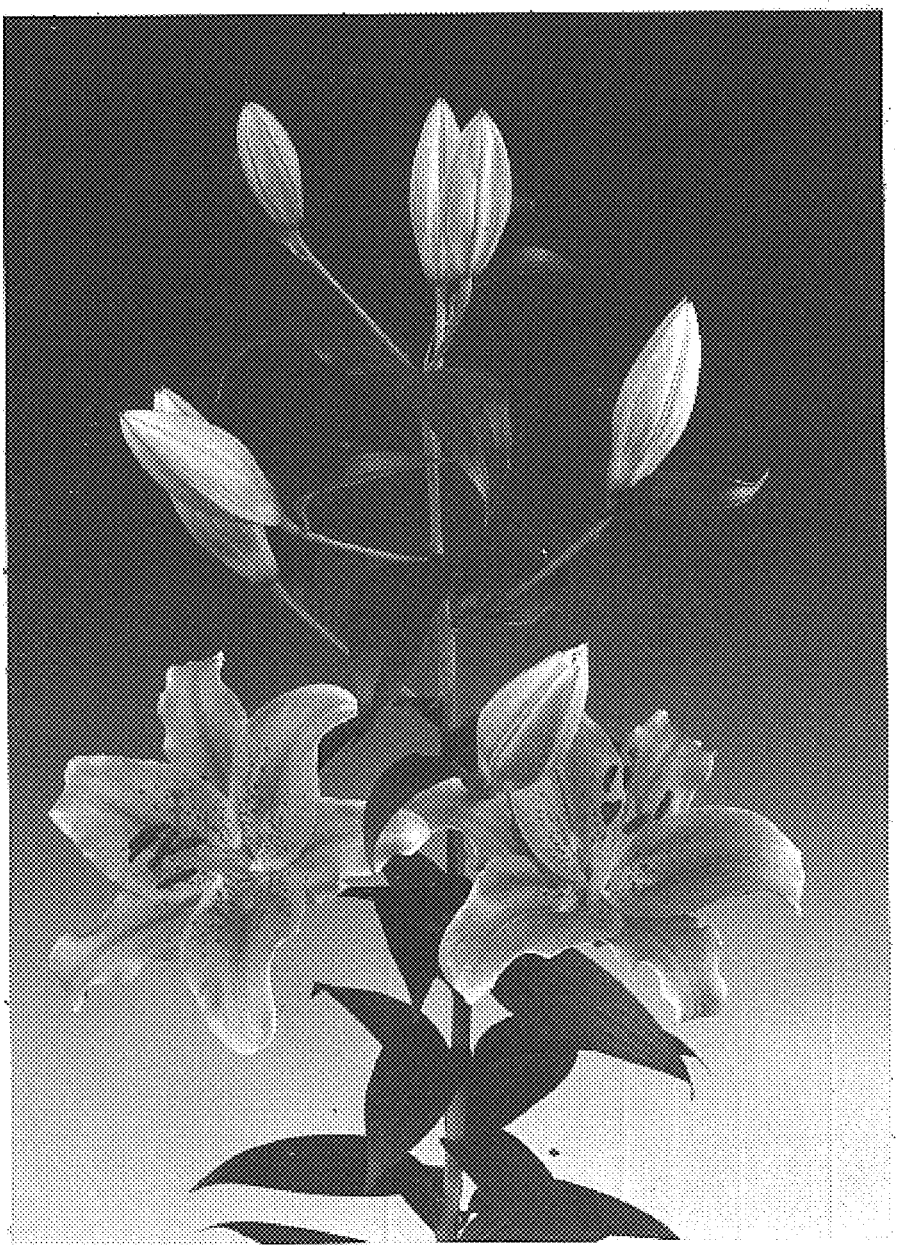

* * * * *